United States Patent [19]

Berg et al.

[11] Patent Number: 5,085,739
[45] Date of Patent: Feb. 4, 1992

[54] SEPARATION OF THE PROPYL ALCOHOLS FROM WATER BY AZEOTROPIC OR EXTRACTIVE DISTILLATION

[75] Inventors: Lloyd Berg, 1314 S. Third Ave., Bozeman, Mont. 59715; Zuyin Yang, Bozeman, Mont.

[73] Assignee: Lloyd Berg, Bozeman, Mont.

[21] Appl. No.: 648,025

[22] Filed: Jan. 30, 1991

[51] Int. Cl.$^5$ .......................... B01D 3/36; B01D 3/40; C07C 29/84

[52] U.S. Cl. .......................... 203/18; 203/57; 203/58; 203/60; 203/62; 203/63; 203/64; 568/916

[58] Field of Search .......................... 203/18, 57, 58, 60, 203/62, 63, 64, 56, 51; 568/916, 918

[56] References Cited

U.S. PATENT DOCUMENTS

| | | | |
|---|---|---|---|
| 2,140,694 | 12/1938 | Evans | 568/916 |
| 2,591,671 | 4/1952 | Catterall | 203/18 |
| 2,614,971 | 10/1952 | Burton | 203/18 |
| 3,464,896 | 9/1969 | Washall | 203/18 |
| 4,366,032 | 12/1982 | Mikitenko et al. | 203/64 |
| 4,400,241 | 8/1983 | Braithwaite et al. | 203/18 |
| 4,592,805 | 6/1986 | Berg et al. | 203/64 |
| 4,631,115 | 12/1986 | Berg et al. | 568/916 |
| 4,636,284 | 1/1987 | English et al. | 203/18 |
| 4,666,560 | 5/1987 | Berg et al. | 203/64 |
| 4,826,576 | 5/1989 | Berg et al. | 568/913 |

*Primary Examiner*—Wilbur Bascomb, Jr.

[57] ABSTRACT

Isopropanol and n-propanol cannot be completely separated from water by conventional distillation or rectification because of the minimum boiling azeotrope. Isopropanol and n-propanol can be readily separated from water by using azeotropic or extractive distillation. Typical examples of effective agents are: for isopropanol by azeotropic distillation, vinyl n-butyl ether; by extractive distillation, polyethylene glycol; for n-propanol by azeotropic distillation, amyl formate; by extractive distillation, n-butyl acetate.

4 Claims, No Drawings

SEPARATION OF THE PROPYL ALCOHOLS FROM WATER BY AZEOTROPIC OR EXTRACTIVE DISTILLATION

FIELD OF THE INVENTION

This invention relates to a method for separating n-propanol or isopropanol from water using certain organic compounds as the agent in azeotropic or extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and this make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Celcius degrees or more higher than the lowest boiling component.

At the bottom of a continuous column, the less volatile components of the close boiling mixtures and the extractive agent are continuously removed from the colum. The usual methods of separation of these two components are the use of another rectification column, cooling and phase separation or solvent extraction.

Isopropanol, B.P.=82.3° C. forms a minimum boiling azeotrope with water at 80.3° C. containing 12.6% water. n-Propanol, B.P.=97.3° C. forms a minimum boiling azeotrope with water boiling at 87° C. containing 28% water. The alcohol-water azeotrope is impossible to separate by distillation because the relative volatility is 1.0. Extractive distillation would be an attractive method of effecting the separation of isopropanol or n-propanol from water if agents can be found that (1) will enhance the relative volatility between the propyl alcohols and water and (2) are easy to recover, that is, form no azeotrope with water or propyl alcohol and boil sufficiently above these to make separation by rectification possible with only a few theoretical plates. Azeotropic distillation would also be an attractive method of separating these two if agents can be found that will enhance the relative volatility sufficiently.

The advantage of using azeotropic or extractive distillation in this separation can be seen from the data presented in Table 1 below.

TABLE 1

| Theoretical And Actual Plates Required vs. Relative Volatility | | |
|---|---|---|
| Relative Volatility | Theoretical Plates Required At Total Reflux, 99% Purity | Actual Plates Required, 75% Eff. |
| 1.2 | 52 | 70 |
| 1.5 | 23 | 31 |
| 2.0 | 13 | 17 |
| 2.5 | 10 | 13 |

The relative volatility of the propyl alcohols-water azeotropes is 1 and thus cannot be separated by conventional rectification. Plates possessing an efficiency of 75% are commonly employed. Several of the agents that we have discovered yield a relative volatility of 2.0 or higher which would require a plate requirement of only 17.

Extractive distillation typically requires the addition of an equal amount to twice as much extractive agent as the propanol-water mixture on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable also that the extractive agent be miscible with the propanol otherwise it will form a two-phase azeotrope with the propanol in the recovery column and some other method of separation will have to be employed.

OBJECTIVE OF THE INVENTION

This objects of this invention are to provide a process or method of azeotropic or extractive distillation that will enhance the relative volatility of isopropanol or n-propanol from water in their separation in a rectification column. It is a further object of this invention to identify organic compounds that are stable, can be separated from the propyl alcohol by rectification with relatively few plates and can be recycled to the extractive distillation column with little decomposition.

SUMMARY OF THE INVENTION

The objects of this invention are provided by a process for the separation of isopropanol or n-propanol from water which entails the use of certain organic compounds as the agent in azeotropic or extractive distillation.

DETAILED DESCRIPTION OF THE INVENTION

We have discovered that certain organic compounds will effectively increase the relative volatility between isopropanol or n-propanol and water and permit the separation of the propanols from water by rectification when employed as the agent in extractive distillation. Table 2 lists the agents that we have found to be effective extractive distillation agents to recover water as the overhead from isopropanol. The data in Table 2, 3, 5, 6 and 7 were obtained in a vapor-liquid equilibrium still.

In every case, the starting material was the propanol-water azeotrope. The relative volatilities are listed for each of the agents. The compounds which are effective extractive distillation agents to remove water as overhead from isopropanol are 1-butanol, 2-butanol, t-amyl alcohol, methyl benzoate, 3-methyl-1-butanol, butyl benzoate, 3-pentanone, 4-methyl-2-pentanone, 2-pentanone, methyl isoamyl ketone, 3-methyl-2-butanone, ethylene glycol methyl ether, n-butyl acetate, n-amyl acetate, isobutyl acetate, propyl butyrate, isobutyl isobutyrate, n-hexyl formate, butyl butyrate, ethyl butyrate, ethyl caproate, hexyl acetate, mesityl oxide, 2-undecanone, 3-octanone, propylene glycol isobutyl ether, 2-heptanone, 4-methyl-2-pentanone, n-butyl ether, vinyl n-butyl ether, vinyl isobutyl ether, benzyl ether, propiophenone, nitrobenzene, n-decanol,2-octanol, hexyl alcohol, 1,5-pentanediol, diethylene glycol, polyethylene glycol 300, anisole and polyethylene glycol 400.

Table 3 lists a number of compounds that proved to be ineffective as extractive distillation agents in the separation of isopropanol from water.

Four of the agents whose relative volatilities had been determined in the vapor-liquid equilibrium still were then evaluated in a glass perforated plate rectification column possessing 7.3 theoretical plates and the results listed in Table 4. Vinyl n-butyl ether was evaluated in the azeotropic distillation mode and gave a relative volatility of 1.33. n-Butanol, 4-methyl-2-pentanone and polyethylene glycol 300 were evaluated in the extractive distillation mode and yielded relative volatilities of 1.20, 1.45 and 1.57 respectively.

Table 5 lists the agents that we have found to be effective extractive distillation agents to recover water as the overhead product from n-propanol. They are anisole, nitrobenzene, methyl benzoate, n-hexyl alcohol, alpha-methyl benzyl alcohol, undecyl alcohol, isodecyl alcohol, cyclododecanol, dipropylene glycol methyl ether, butoxypropanol, propoxypropanol, n-butyl acetate, isobutyl acetate, 2-heptanone, diethylene glycol ethyl ether acetate, ethylene glycol ethyl ether acetate, ethylene glycol, 1,5-pentanediol, 1,6-hexanediol, hexylene glycol, polyethylene glycol 200 and ethylene carbonate.

TABLE 2

Effective Agents For Separating Isopropanol From Water

| Compounds | Relative Volatility |
|---|---|
| 1-Butanol | 1.43 |
| 2-Butanol | 1.36 |
| t-Amyl alcohol | 1.28 |
| Methyl benzoate | 1.50 |
| 3-Methyl-1-butanol | 1.54 |
| Butyl benzoate | 1.36 |
| 3-Pentanone | 1.45 |
| 4-Methyl-2-pentanone | 1.36 |
| 2-Pentanone | 1.38 |
| Methyl isoamyl ketone | 1.32 |
| 3-Methyl-2-butanone | 1.24 |
| Ethylene glycol methyl ether | 1.60 |
| n-Butyl acetate | 1.28 |
| n-Amyl acetate | 1.30 |
| Isobutyl acetate | 1.24 |
| Propyl butyrate | 1.72 |
| Isobutyl isobutyrate | 1.61 |
| n-Hexyl formate | 1.52 |
| Butyl butyrate | 1.39 |
| Ethyl butyrate | 1.46 |
| Ethyl caproate | 1.56 |
| Hexyl acetate | 1.31 |
| Mesityl oxide | 1.47 |
| Propylene glycol isobutyl ether | 1.29 |
| 2-Undecanone | 1.26 |
| 3-Octanone | 1.22 |
| 2-Heptanone | 1.32 |
| 4-Methyl-2-pentanone | 1.36 |
| n-Butyl ether | 1.49 |
| Vinyl n-butyl ether | 1.83 |
| Vinyl isobutyl ether | 1.57 |
| Benzyl ether | 1.41 |
| Propiophenone | 1.31 |
| Nitrobenzene | 1.32 |
| n-Decanol | 1.38 |
| 2-Octanol | 1.30 |
| Hexyl alcohol | 1.32 |
| 1,5-Pentanediol | 1.22 |
| Diethylene glycol | 1.80 |
| Polyethylene glycol 300 | 1.56 |
| Polyethylene glycol 400 | 1.26 |
| Anisole | 1.54 |

TABLE 3

Ineffective Agents For Separating Isopropanol From Water

| | |
|---|---|
| Ethyl salicylate | Ethyl acetate |
| Dipropylene glycol dibenzoate | Ethylene glycol methyl ether acetate |
| 4-Methyl pentyl acetate | Isobornyl acetate |
| 1,4-Dioxane | Methyl valerate |
| Propoxypropanol | Diethylene glycol diethyl ether |
| Diacetone alcohol | Dipropylene glycol dimethyl ether |
| Isobutyl heptyl ketone | |
| Dipropylene glycol methyl ether | 4-Methoxy-4-methyl pentanone-2 |
| 2-Methoxy ethyl ether | Ethylene glycol ethyl ether acetate |
| Tetrahydro furfuryl alcohol | |
| Benzonitrile | Ethylene glycol methyl ether acetate |
| Propylene glycol | |
| 1,4-Butanediol | Dipropylene glycol methyl ether acetate |
| Hexylene glycol | |
| 1,2-Butanediol | Diethylene glycol butyl ether |
| Adiponitrile | 1,6-Hexanediol |
| | 2-Methyl-1,3-propanediol |
| | Dipropylene glycol |
| | 1,3-Butanediol |

TABLE 4

Data From Runs Made In Rectification Column - Isopropanol From Water

| Agent | Column | Time hrs. | Weight % Isopropanol | Weight % Water | Weight % Agent | Relative Volatility | Mode |
|---|---|---|---|---|---|---|---|
| Vinyl n-butyl ether | Overhead | 8 | 28.5 | 14.5 | 57.0 | 1.33 | Azeotropic |
| | Bottoms | | 80.3 | 5.1 | 14.6 | | |
| n-Butanol | Overhead | 2 | 65.3 | 34.7 | — | 1.20 | Extractive |
| | Bottoms | | 87.9 | 12.1 | | | |
| 4-Methyl-2-pentanone | Overhead | 2 | 23.2 | 76.8 | — | 1.45 | Extractive |
| | Bottoms | | 82.3 | 17.7 | | | |
| Polyethylene glycol 300 | Overhead | 2 | 95.9 | 4.1 | — | 1.57 | Extractive |
| | Bottoms | | 47.1 | 52.9 | | | |

TABLE 5

Effective Agents For Separating n-Propanol From Water - Extractive Distn.

| Compounds | Relative Volatility |
| --- | --- |
| Anisole | 2.0 |
| Nitrobenzene | 1.21 |
| Methyl benzoate | 1.70 |
| n-Hexyl alcohol | 1.44 |
| alpha-Methyl benzyl alcohol | 1.48 |
| Undecyl alcohol | 1.39 |
| Isodecyl alcohol | 1.30 |
| Cyclododecanol | 1.43 |
| Dipropylene glycol methyl ether | 1.43 |
| Butoxypropanol | 2.2 |
| Propoxypropanol | 1.5 |
| n-Butyl acetate | 1.7 * |
| Isobutyl acetate | 1.3 * |
| Diethylene glycol ethyl ether acetate | 1.3 |
| Ethylene glycol ethyl ether acetate | 1.37 |
| 2-Heptanone | 1.88 |
| Ethylene glycol | 1.7 * |
| 1,5-Pentanediol | 1.22 |
| 1,6-Hexanediol | 1.31 |
| Hexylene glycol | 1.20 |
| Polyethylene glycol 200 | 1.33 * |
| Ethylene carbonate | 1.3 * |

* Brings n-propanol out as overhead

TABLE 6

Effective Agents For Separating n-Propanol From Water - Azeotropic Distn.

| Compounds | Relative Volatility |
| --- | --- |
| Benzonitrile | 1.5 |
| n-Butyl ether | 2.6 |
| Vinyl n-butyl ether | 3.0 |
| Vinyl isobutyl ether | 2.7 |
| 4-Methyl-2-pentanone | 1.3 |
| Mesityl oxide | 1.2 |
| Propyl butyrate | 3.6 |
| Isobutyl butyrate | 1.2 |
| Hexyl acetate | 3.4 |
| Amyl acetate | 1.5 |
| Nonyl alcohol | 1.8 |
| 3-Heptanone | 4.3 |

Table 6 lists the agents that we have found to be effective azeotrope formers to recover water as the overhead product from n-propanol. They are benzonitrile, n-butyl ether, vinyl n-butyl ether, vinyl isobutyl ether, 4-methyl-2-pentanone, mesityl oxide, propyl butyrate, isobutyl butyrate, hexyl acetate, amyl acetate, nonyl alcohol and 3-heptanone.

Table 7 lists a number of compounds that proved to be ineffective as extractive distillation agents in the separation of n-propanol from water.

Seven of the agents whose relative volatility had been determined in the vapor-liquid equilibrium still were then evaluated in the glass perforated plate column and the results listed in Table 8. Amyl formate was evaluated in the azeotropic distillation mode and gave a relative volatility of 1.23. Butoxypropanol, propoxypropanol, n-butyl acetate, isobutyl acetate, 4-methyl-2-pentanone and 1,6-hexanediol were evaluated in the extractive distillation mode and yielded relative volatilities of 1.26, 1.21, 1.32, 1.21, 1.45 and 1.11 respectively. n-Butyl acetate and isobutyl acetate bring the n-propanol off as overhead and the water as bottoms product.

THE USEFULNESS OF THE INVENTION

The usefulness or utility of this invention can be demonstrated by referring to the data presented in Tables 2 to 8. All of the successful agents show that isopropanol or n-propanol can be separated from water by means of azeotropic or extractive distillation in a rectification column and that the ease of separation as measured by relative volatility is considerable.

WORKING EXAMPLES

Example 1

Forty grams of the isopropanol-water azeotrope and 20 grams of propyl butyrate were charged to a vapor-liquid equilibrium still and refluxed for six hours. Analysis indicated a vapor composition of 22.9% water, 77.1% isopropanol; a liquid composition of 14.7% water, 85.3% isopropanol which is a relative volatility of 1.72.

Example 2

A solution comprising 175 grams of isopropanol and 25 grams of water was placed in the stillpot of a 7.3 theoretical plate perforated plate column. When refluxing began, an extractive agent comprising poly ethylene glycol 300 was pumped into the column at a rate of 15 ml/min. The temperature of the extractive agent as it entered the column was 75° C. After establishing the feed rate of the extractive agent, the heat input to the isopropanol-water in the stillpot was adjusted to give a total reflux rate of 40 ml/min.

TABLE 7

Ineffective Agents For Separating n-Propanol From Water

| | |
| --- | --- |
| Benzyl ether | Isobutyl heptyl ketone |
| 3-Pentanone | Propiophenone |
| n-Decanol | Diethylene glycol diethyl ether |
| 2-Octanol | n-Propyl acetate |
| 1,4-Butanediol | 2-Methyl pyrrolidone |
| Propylene glycol | Triethylene glycol |
| Dipropylene glycol | Diethylene glycol |
| 1,3-Butanediol | Polyethylene glycol 300 |
| 1,2-Butanediol | Tripropylene glycol |
| Adiponitrile | Polyethylene glycol 400 |
| Propylene carbonate | 2-Methyl-2,4-pentanediol |

TABLE 8

Data From Runs Made In Rectification Column - n-Propanol From Water

| Agent | Column | Time hrs. | Weight % Water | Weight % n-Propanol | Weight % Agent | Relative Volatility | Mode |
| --- | --- | --- | --- | --- | --- | --- | --- |
| Amyl Formate | Overhead | 4 | 40.3 | 29.9 | 29.8 | 1.23 | Azeotropic |
| | Bottoms | | 7.3 | 25.7 | 67.0 | | |
| Butoxypropanol | Overhead | 2 | 50.1 | 49.9 | — | 1.26 | Extractive |
| | Bottoms | | 15.9 | 84.1 | | | |
| Propoxypropanol | Overhead | 2 | 63.5 | 36.5 | — | 1.21 | Extractive |
| | Bottoms | | 30 | 70 | | | |
| n-Butyl acetate | Overhead | 2 | 27.7 | 72.3 | — | 1.32 * | Extractive |
| | Bottoms | | 73.7 | 26.3 | | | |
| Isobutyl acetate | Overhead | 2 | 26.1 | 73.9 | — | 1.21 * | Extractive |

TABLE 8-continued

| | Data From Runs Made In Rectification Column - n-Propanol From Water | | | | | | |
|---|---|---|---|---|---|---|---|
| Agent | Column | Time hrs. | Weight % Water | Weight % n-Propanol | Weight % Agent | Relative Volatility | Mode |
| | Bottoms | | 58.8 | 41.2 | | | |
| 1,6-Hexanediol | Overhead | 2 | 38.6 | 61.4 | — | 1.11 | Extractive |
| | Bottoms | | 23.6 | 76.4 | | | |

* n-Propanol comes off as overhead.

After two hours of operation, the overhead and bottoms samples of approximately two ml. were collected and analysed by gas chromatography. The overhead analysis was 95.9% isopropanol, 4.1% water and the bottoms analysis was 47.1% isopropanol, 52.9% water. Using these compositions in the Fenske equation, with the number of theoretical plates in the column being 7.3, gave an average relative volatility of 1.57 for each theoretical plate. This data is presented in Table 4.

Example 3

Forty grams of the n-propanol-water azeotrope and 30 grams of butoxypropanol were charged to the vapor-liquid equilibrium still and refluxed for four hours. Analysis indicated a vapor composition of 39.5% water, 60.5% n-propanol; a liquid composition of 22.8% water, 77.2% n-propanol which is a relative volatility of 2.2.

Example 4

A solution comprising 288 grams of n-propanol and 112 grams of water was placed in the stillpot of the perforated plate column. When refluxing began, an extractive agent comprising n-butyl acetate was pumped into the column at a rate of 15/min/ml. The temperature of the extractive agent as it entered the column was 85° C. After establishing the feed rate of the extractive agent, the heat input to the n-propanol-water in the stillpot was adjusted to give a total reflux rate of 40 ml/min. After two hours of operation, the overhead and bottoms samples of approximately two ml. were collected and analysed. The overhead analysis was 72.3% n-propanol, 27.7% water and the bottoms analysis was 26.3% n-propanol, 73.7% water. This gives an average relative volatility of 1.32 for each theoretical plate. This data is presented in Table 8.

Example 5

Eighty grams of the n-propanol-water azeotrope and 30 grams of n-amyl acetate as the azeotrope former were charged to the vapor-liquid equilibrium still and refluxed for 14 hours. Analysis indicated a vapor composition of 42% water, 58% n-propanol; a liquid composition of 32.7% water, 67.3% n-propanol which is a relative volatility of 1.5.

Example 6

Two hundred grams of the n-propanol-water azeotrope and 85 grams of n-amyl formate as the azeotrope former were charged to the 7.3 theoretical plate column and refluxed at total reflux for four hours. Analysis indicated a vapor composition of 40.3% water, 29.9% n-propanol, 29.8% n-amyl formate; a liquid composition of 7.3% water, 25.7% n-propanol and 67% n-amyl formate. This gives an average relative volatility of 1.23 for each theoretical plate. This data is presented in Table 8.

We claim:

1. A method for recovering isopropanol from a mixture of isopropanol and water which comprises distilling a mixture of isopropanol and water in the presence of about one part of an extractive agent per part of isopropanol-water mixture, recovering water as the overhead product and obtaining the isopropanol and the extractive agent from the stillpot, wherein said extractive agent consists of one material selected from the group consisting of methyl benzoate, butyl benzoate, 3-pentanone, 4-methyl-2-pentanone, 2-pentanone, methyl isoamyl ketone, n-butyl acetate, 3-methyl-2-butanone, ethylene glycol methyl ether, n-amyl acetate, isobutyl acetate, propyl butyrate, isobutyl isobutyrate, n-hexyl formate, butyl butyrate, ethyl butyrate, ethyl caproate, hexyl acetate, mesityl oxide, propylene glycol isobutyl ether, 2-undecanone, 3-octanone, 2-heptanone, propiophenone, and nitrobenzene.

2. A method for recovering n-propanol from a mixture of n-propanol and water which comprises distilling a mixture of n-propanol and water in the presence of about one part of an extractive agent per part of n-propanol-water mixture, recovering the water as overhead product and obtaining the n-propanol and the extractive agent from the stillpot, wherein said extractive agent comprises one material selected from the group consisting of nitrobenzene, methyl benzoate, butoxypropanol, propoxypropanol, diethylene glycol ethyl ether acetate, 2-heptanone, and ethylene glycol ethyl ether acetate.

3. A method for recovering n-propanol from a mixture of n-propanol and water which comprises distilling a mixture of n-propanol and water in the presence of about one part of an extractive agent per part of n-propanol-water mixture, recovering the n-propanol as overhead product and obtaining the water and the extractive agent from the stillpot, wherein said extractive agent consists of one material selected from the group consisting of n-butyl acetate, isobutyl acetate, and ethylene carbonate.

4. A method for recovering n-propanol from a mixture of n-propanol and water which comprises distilling a mixture of n-propanol and water in the presence of an azeotrope forming agent, recovering the water and the azeotrope forming agent as overhead product and obtaining the n-propanol from the stillpot, wherein said azeotrope forming agent comprises one material selected from the group consisting of benzonitrile, mesityl oxide, hexyl acetate, amyl acetate, 3-heptanone, propyl butyrate, 4-methyl-2-pentanone and isobutyl butyrate.

* * * * *